(12) United States Patent
Schmidt et al.

(10) Patent No.: US 10,080,887 B2
(45) Date of Patent: Sep. 25, 2018

(54) LEADLESS CARDIAC PACING DEVICES INCLUDING TISSUE ENGAGEMENT VERIFICATION

(71) Applicant: Cardiac Pacemakers, Inc., St. Paul, MN (US)

(72) Inventors: Brian L. Schmidt, White Bear Lake, MN (US); Benjamin J. Haasl, Forest Lake, MN (US); John M. Edgell, Plymouth, MN (US); Dana Sachs, Pine City, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 674 days.

(21) Appl. No.: 14/698,537

(22) Filed: Apr. 28, 2015

(65) Prior Publication Data
US 2015/0306378 A1  Oct. 29, 2015

Related U.S. Application Data

(60) Provisional application No. 61/985,826, filed on Apr. 29, 2014.

(51) Int. Cl.
*A61N 1/05* (2006.01)
*A61B 19/00* (2006.01)
(Continued)

(52) U.S. Cl.
CPC ............... *A61N 1/059* (2013.01); *A61B 6/12* (2013.01); *A61B 90/39* (2016.02); *A61N 1/0573* (2013.01);
(Continued)

(58) Field of Classification Search
CPC ... A61B 2090/3966; A61B 6/12; A61B 90/39; A61N 1/0573; A61N 1/059; A61N 1/37205; A61N 1/3756
See application file for complete search history.

(56) References Cited

U.S. PATENT DOCUMENTS 721,869 A   3/1903  Dunning
3,717,151 A  2/1973  Collett
(Continued)

FOREIGN PATENT DOCUMENTS

CA   1003904 A1  1/1977
DE   2053919 A1  5/1972
(Continued)

OTHER PUBLICATIONS

Spickler, et al. "Totally Self-Contained Intracardiac Pacemaker" J. Electrocardiology, vol. 3, Nos. 3 & 4, pp. 325-331 (1970).

*Primary Examiner* — Michael Rozanski
(74) *Attorney, Agent, or Firm* — Seager, Tufte & Wickhem LLP

(57) ABSTRACT

An implantable leadless cardiac pacing device including a housing having a proximal end and a distal end, an electrode positioned proximate the distal end of the housing configured to be positioned adjacent cardiac tissue, and a tissue anchoring member extending from the distal end of the housing configured to secure the housing to cardiac tissue. The device further includes a tissue engagement verification feature configured to provide feedback upon engagement of the tissue anchoring member in cardiac tissue.

20 Claims, 14 Drawing Sheets

(51) Int. Cl.
  *A61B 6/12*     (2006.01)
  *A61N 1/375*    (2006.01)
  *A61N 1/372*    (2006.01)
  *A61B 90/00*    (2016.01)

(52) U.S. Cl.
  CPC ....... *A61N 1/3756* (2013.01); *A61N 1/37205* (2013.01); *A61B 2090/3966* (2016.02)

(56) References Cited

U.S. PATENT DOCUMENTS

| | | |
|---|---|---|
| 3,754,555 A | 8/1973 | Schmitt |
| 3,814,104 A | 6/1974 | Irnich et al. |
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,662,382 A | 5/1987 | Sluetz et al. |
| 4,898,577 A | 2/1990 | Badger et al. |
| 4,913,164 A | 4/1990 | Greene et al. |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardnier et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,743,240 B2 | 6/2004 | Smith et al. |
| 6,755,812 B2 | 6/2004 | Peterson et al. |
| 6,909,920 B2 | 6/2005 | Lokhoff et al. |
| 6,944,507 B2 | 9/2005 | Fröberg et al. |
| 6,953,454 B2 | 10/2005 | Peterson et al. |
| 7,027,876 B2 | 4/2006 | Casavant et al. |
| 7,082,335 B2 | 7/2006 | Klein et al. |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings et al. |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |
| 7,904,179 B2 | 3/2011 | Ruffen et al. |
| 7,920,928 B1 | 4/2011 | Yang et al. |
| 7,993,351 B2 | 8/2011 | Worley et al. |
| 8,010,209 B2 | 8/2011 | Jacobson |
| 8,036,757 B2 | 10/2011 | Worley |
| 8,057,486 B2 | 11/2011 | Hansen |

(56) References Cited

U.S. PATENT DOCUMENTS

| | | |
|---|---|---|
| 8,082,035 B2 | 12/2011 | Glukhovsky |
| 8,103,361 B2 | 1/2012 | Moser |
| 8,108,054 B2 | 1/2012 | Helland |
| 8,142,347 B2 | 3/2012 | Griego et al. |
| 8,160,722 B2 | 4/2012 | Rutten et al. |
| 8,185,213 B2 | 5/2012 | Kveen et al. |
| 8,219,213 B2 | 7/2012 | Sommer et al. |
| 8,233,994 B2 | 7/2012 | Sommer et al. |
| 8,252,019 B2 | 8/2012 | Fleming, III |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,428,750 B2 | 4/2013 | Kolberg |
| 8,452,420 B2 | 5/2013 | Flach et al. |
| 8,478,431 B2 | 7/2013 | Griswold et al. |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan et al. |
| 8,634,912 B2 | 1/2014 | Bornzin et al. |
| 8,670,842 B1 | 3/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 2002/0077556 A1 | 6/2002 | Schwartz |
| 2003/0004537 A1 | 1/2003 | Boyle et al. |
| 2004/0116992 A1 | 6/2004 | Wardle et al. |
| 2004/0176797 A1 | 9/2004 | Opolski |
| 2005/0090890 A1 | 4/2005 | Wu et al. |
| 2005/0267555 A1 | 12/2005 | Marnfeldt et al. |
| 2006/0247753 A1 | 11/2006 | Wenger et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2009/0082828 A1 | 3/2009 | Ostroff |
| 2009/0281605 A1 | 11/2009 | Marnfeldt et al. |
| 2010/0198288 A1 | 8/2010 | Ostroff |
| 2011/0034939 A1 | 2/2011 | Kveen et al. |
| 2011/0112548 A1 | 5/2011 | Fifer et al. |
| 2011/0125163 A1 | 5/2011 | Rutten et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103049 A1 | 4/2013 | Bonde |
| 2013/0116740 A1* | 5/2013 | Bornzin ............... A61N 1/3756 607/9 |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0148815 A1 | 5/2014 | Wenzel et al. |
| 2014/0180306 A1 | 6/2014 | Grubac et al. |
| 2015/0025612 A1 | 1/2015 | Haasl et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |

FOREIGN PATENT DOCUMENTS

| | | |
|---|---|---|
| EP | 779080 B1 | 5/2003 |
| JP | 05245215 A | 9/1993 |
| WO | 03032807 A2 | 4/2003 |
| WO | 2009039400 A1 | 3/2009 |
| WO | 2012092067 A1 | 7/2012 |
| WO | 2012092074 A1 | 7/2012 |

* cited by examiner

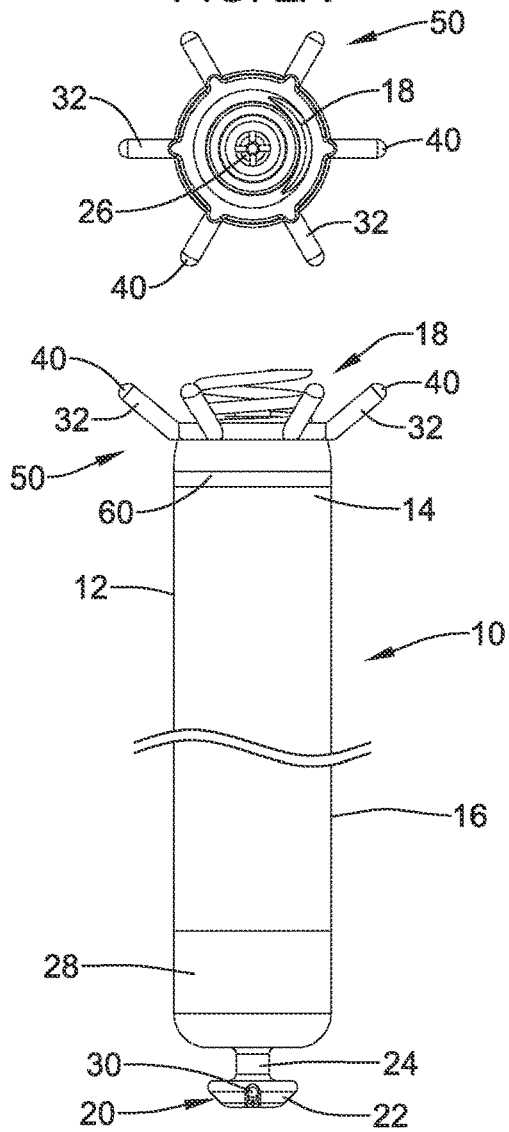
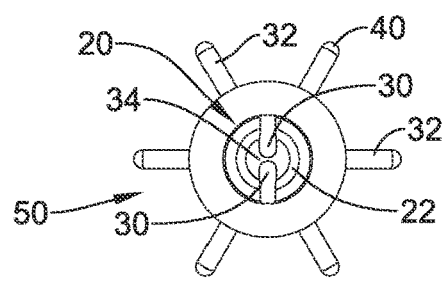

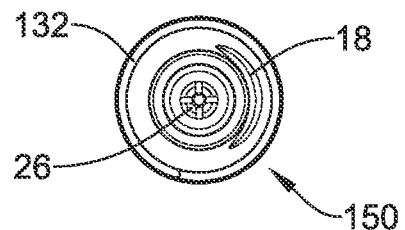
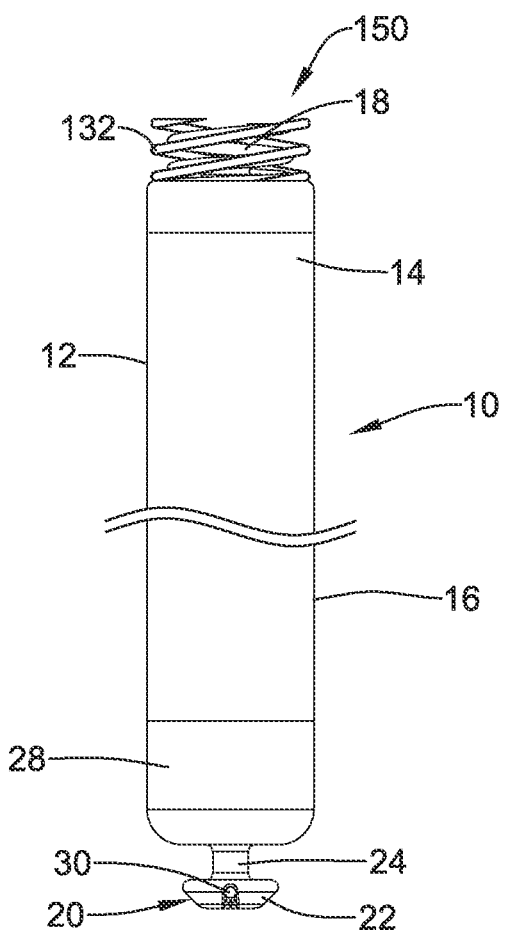

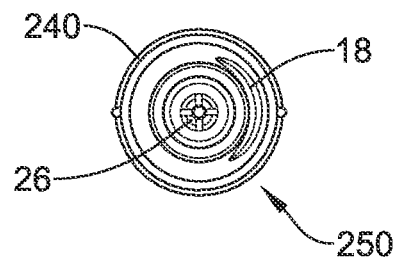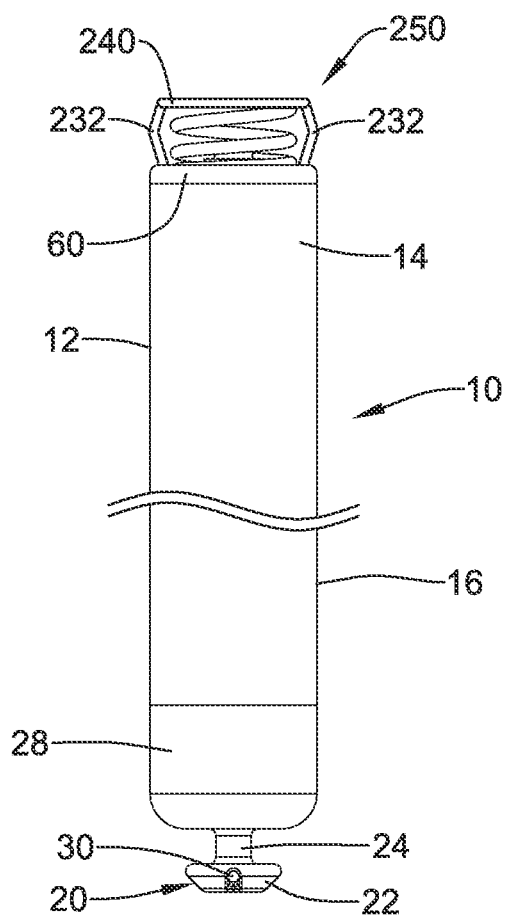

LEADLESS CARDIAC PACING DEVICES INCLUDING TISSUE ENGAGEMENT VERIFICATION

CROSS REFERENCE TO RELATED APPLICATIONS

This application claims the benefit of U.S. Provisional Application Ser. No. 61/985,826, filed Apr. 29, 2014, the disclosure of which is incorporated herein in its entirety.

TECHNICAL FIELD

The present disclosure pertains to medical devices, and methods for manufacturing medical devices. More particularly, the present disclosure pertains to leadless cardiac pacing devices including tissue engagement verification features.

BACKGROUND

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically including bipolar pacing/sensing electrodes, a power source (e.g. a battery), and associated electrical circuitry for controlling the pacing/sensing electrodes, and thus provide electrical stimulation to heart tissue and/or sense a physiological condition. The small capsule is typically fixed to an intracardiac implant site in a cardiac chamber with a fixation mechanism engaging the intracardiac tissue.

Accordingly, it is desirable to provide alternative structures to facilitate verification of sufficient engagement of the fixation mechanism into the intracardiac tissue to ensure the leadless cardiac pacemaker is secured to the intracardiac tissue.

SUMMARY

The disclosure is directed to several alternative designs, materials and methods of manufacturing medical device structures and assemblies, and uses thereof.

Accordingly one illustrative embodiment is an implantable leadless cardiac pacing device including a housing having a proximal end and a distal end, an electrode positioned proximate the distal end of the housing configured to be positioned adjacent cardiac tissue, and a tissue anchoring member extending from the distal end of the housing configured to secure the housing to cardiac tissue. The device further includes a tissue engagement verification feature configured to provide feedback upon engagement of the tissue anchoring member in cardiac tissue.

Another illustrative embodiment is an implantable leadless cardiac pacing device including a housing having a proximal end and a distal end, an electrode positioned proximate the distal end of the housing configured to be positioned adjacent cardiac tissue, and a tissue anchoring member extending from the distal end of the housing configured to secure the housing to cardiac tissue. The device further includes a radiopaque marker movable relative to the housing and a radiopaque reference point stationary relative to the housing. Displacement of the radiopaque marker relative to the radiopaque reference point provides visual feedback of engagement of the tissue anchoring member in cardiac tissue.

Yet another illustrative embodiment is a method of implanting a leadless cardiac pacing device. The method includes advancing the leadless cardiac pacing device into a chamber of a heart. A tissue anchoring member of the leadless cardiac pacing device is then engaged into cardiac tissue. While engaging the tissue anchor member into the cardiac tissue, displacement of a radiopaque marker of the leadless cardiac pacing device relative to a radiopaque reference point is fluoroscopically observed to confirm engagement of the tissue anchoring member in cardiac tissue.

The above summary of some example embodiments is not intended to describe each disclosed embodiment or every implementation of the aspects of the disclosure.

BRIEF DESCRIPTION OF THE DRAWINGS

The disclosure may be more completely understood in consideration of the following detailed description in connection with the accompanying drawings, in which:

FIG. 2 is a side view of an exemplary leadless pacing device;

FIG. 2A is a distal end view of the leadless pacing device shown in FIG. 2;

FIG. 2B is a proximal end view of the leadless pacing device shown in FIG. 2;

FIG. 4A is a side view of another exemplary leadless pacing device;

FIG. 4B is a distal end view of the leadless pacing device shown in FIG. 4A;

FIG. 6A is a side view of another exemplary leadless pacing device;

FIG. 6B is a distal end view of the leadless pacing device shown in FIG. 6A;

Figure 1:
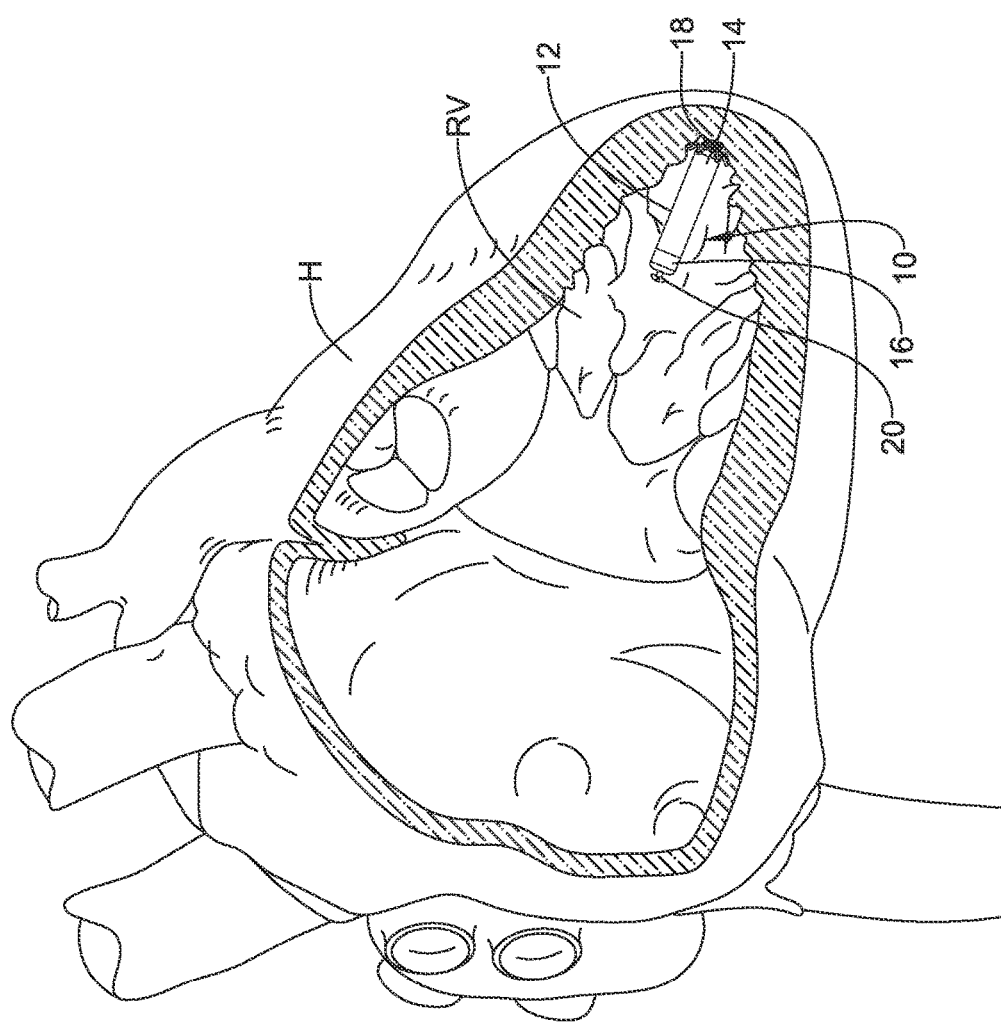
FIG. 1 is a plan view of an exemplary leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. A leadless cardiac pacemaker may take the form of a relatively small capsule that may be fixed to an intracardiac implant site in a cardiac chamber. It can be readily appreciated that the implantation of a leadless pacing device within a beating heart can be difficult. Accordingly, it may be desirable for a leadless pacing device to include a tissue engagement verification feature to facilitate verification of sufficient engagement of the fixation mechanism into the intracardiac tissue to ensure the leadless cardiac pacemaker is secured to the intracardiac tissue.

FIG. 1 illustrates an example implantable leadless cardiac pacing device 10 implanted in a chamber of a heart H such as, for example, the right ventricle RV. The device 10 may include a shell or housing 12 having a distal region 14 and a proximal region 16. One or more anchoring members 18 may be disposed adjacent to the distal region 14. The anchoring member 18 may be used to attach the device 10 to a tissue wall of the heart H, such as intracardiac tissue, or otherwise anchor the implantable device 10 to the anatomy of the patient. A docking member 20 may be disposed adjacent to the proximal region 16 of the housing 12. The docking member 20 may be utilized to facilitate delivery and/or retrieval of the implantable device 10.

Some of the features of the device 10 can be seen in FIG. 2, FIG. 2A, and FIG. 2B. For example, the device 10 may include a first electrode 26 positioned adjacent to the distal region 14 of the housing 12. A second electrode 28 may also be defined along the housing 12. For example, the housing 12 may include a conductive material and may be insulated along a portion of its length. A section along the proximal region 16 may be free of insulation so as to define the second electrode 28. The electrodes 26/28 may be sensing and/or pacing electrodes to provide electro-therapy and/or sensing capabilities. The first electrode 26 may be capable of being positioned against or otherwise contact the cardiac tissue of the heart H while the second electrode 28 may be spaced away from the first electrode 26, and thus spaced away from the cardiac tissue. The device 10 may also include a pulse generator (e.g., electrical circuitry) and a power source (e.g., a battery) within the housing 12 to provide electrical signals to the electrodes 26/28. Electrical communication between the pulse generator and the electrodes 26/28 may provide electrical stimulation to heart tissue and/or sense a physiological condition.

The docking member 20 may include a head portion 22 and a neck portion 24 extending between the housing 12 and the head portion 22. The head portion 22 may be capable of engaging with a delivery and/or retrieval catheter. For example, the head portion 22 may include a bore or opening 30 formed therein. The ends of the bore 30 may be open or exposed while a central region of the bore 30 may be covered by a section the 34 of the head portion 22, for example. During delivery, the device 10 may be secured to a delivery device by extending a suture through the bore 30. Additionally or alternatively, a portion of the delivery catheter may include projections or lugs that may engage the bore 30. Some additional details of example delivery devices for delivering the device 10 to cardiac tissue are disclosed herein.

The docking member 20 may also be engaged if it is desired to retrieve and/or reposition the device 10. For example, a retrieval catheter may be advanced to a position adjacent to the device 10. A retrieval mechanism such as a snare, tether, arm, or other suitable structure may extend from the retrieval catheter and engage the head portion 22. When suitably engaged, the device 10 may be pulled from the cardiac tissue and, ultimately, removed from the patient or repositioned.

As the name suggests, the anchoring member 18 may be used to anchor the device 10 to the target tissue. A suitable number of anchoring members 18 may be used with the device 10. For example, the device 10 may include one, two, three, four, five, six, seven, eight, or more anchoring members. In at least some embodiments, the anchoring member 18 may take the form of a helix or screw. According to these embodiments, the anchoring member 18 may be threaded or rotated into cardiac tissue. In other instances, the anchoring member 18 may include one or more, or a plurality of tines configured to be anchored into the cardiac tissue. Some additional details of example mechanisms for threading/anchoring the device 10 to cardiac tissue are disclosed herein.

It can be appreciated that in order to securely anchor the device 10 to cardiac tissue with a helical anchoring member 18 or other anchoring member, it may be desirable to provide intraoperative verification of sufficient engagement of the anchoring member 18 into the cardiac tissue to ensure the device 10 is secured to the cardiac tissue. Accordingly, the device 10 may include one or more tissue engagement verification features to provide the medical personnel intraoperative verification of the degree of tissue engagement of the anchoring member 18 during the implantation procedure. Thus, the tissue engagement verification feature may be configured to provide feedback upon engagement of the tissue anchoring member 18 in cardiac tissue. In some embodiments, the tissue engagement verification feature may be movable from a first position relative to the housing 12 to a second position relative to the housing 12. In some instances, the first position may be an equilibrium position, and the second position may be a displaced position through application of an external force, such as through contact with the cardiac tissue. In some embodiments, the tissue engagement verification feature may be arranged with the device 10 such that the tissue engagement verification feature moves toward the proximal end of the housing 12 as the tissue engagement verification feature moves from the first position to the second position. The tissue engagement verification feature may include a radiopaque material to provide intraoperative visual feedback via fluoroscopy during implantation of the device 10 in the heart H. The radiopaque material of the tissue engagement verification feature may be movable relative to the housing 12, such that the movement of the tissue engagement verification feature may be viewed using fluoroscopy during the medical procedure. In some embodiments, the device 10 may include a radiopaque reference point which is stationary relative to the housing 12, such that displacement of the radiopaque material of the tissue engagement verification feature relative to the radiopaque reference point provides visual feedback of engagement of the tissue anchoring member 18 in cardiac tissue.

One exemplary example of tissue engagement verification features which can be included with the device 10 are illustrated in FIG. 2, FIG. 2A and FIG. 2B. Tissue engagement verification features 50 may be fixedly attached to the housing 12 of the device 10. In other words, the tissue engagement verification features 50 may be designed so that during typical use, the tissue engagement verification features 50 remain attached to housing 12. In some embodiments, the tissue engagement verification features 50 may have some freedom of movement relative to the housing 10. For example, the tissue engagement verification features 50 may be capable of pivoting, rotating, or otherwise moving relative to housing 12.

The form of the tissue engagement verification features 50 may vary. For example, the tissue engagement verification features 50 may take the form of tines 32 projecting from housing 12. In some instances, the tines 32 may be symmetrically or asymmetrically arranged around the perimeter of the housing 12 and extend radially outward therefrom. The tines 32 may extend radially from the housing 12 in a distal direction in a first, equilibrium position, shown in FIG. 2.

The tines 32 may be doped with, made of, or otherwise include a radiopaque material. In some instances, the tines 32 may include a radiopaque marker 40, such as at a distal tip of the tines 32, or along another portion of the tines 32. In other instances, the tines 32, or a portion thereof, may be formed of a radiopaque material or be doped with a radiopaque material, and thus serve as the radiopaque marker. Radiopaque materials are understood to be materials capable of producing a relatively bright image on a fluoroscopy screen or another imaging technique during a medical procedure. This relatively bright image aids the user of the device 10 visualizing the radiopaque marker (e.g., the tine 32) using fluoroscopy. Some examples of radiopaque materials can include, but are not limited to, gold, platinum, palladium, tantalum, tungsten alloy, polymer material loaded with a radiopaque filler, and the like.

In some instances, the device 10 may also include a radiopaque reference point 60 which is stationary relative to the housing 12, or be included as part of the housing 12. For example the radiopaque reference point 60 may be a radiopaque ring surrounding the housing 12, or another radiopaque structure on the housing 12, or the material forming the housing 12. Accordingly, displacement of the radiopaque material of the tines 32 relative to the radiopaque reference point 60 may provide visual feedback of engagement of the tissue anchoring member 18 in cardiac tissue.

The tines 32 may have any desired cross-sectional shape, such as a generally circular cross-sectional shape. In at least some embodiments, the tines 32 may be substantially straight. In other embodiments, the tines 32 may include one or more curves or bends. A variety of other shapes, forms, and configurations are also contemplated for the tines 32. In addition, some devices may include combinations of differently shaped or oriented tines 32.

Figure 3A:
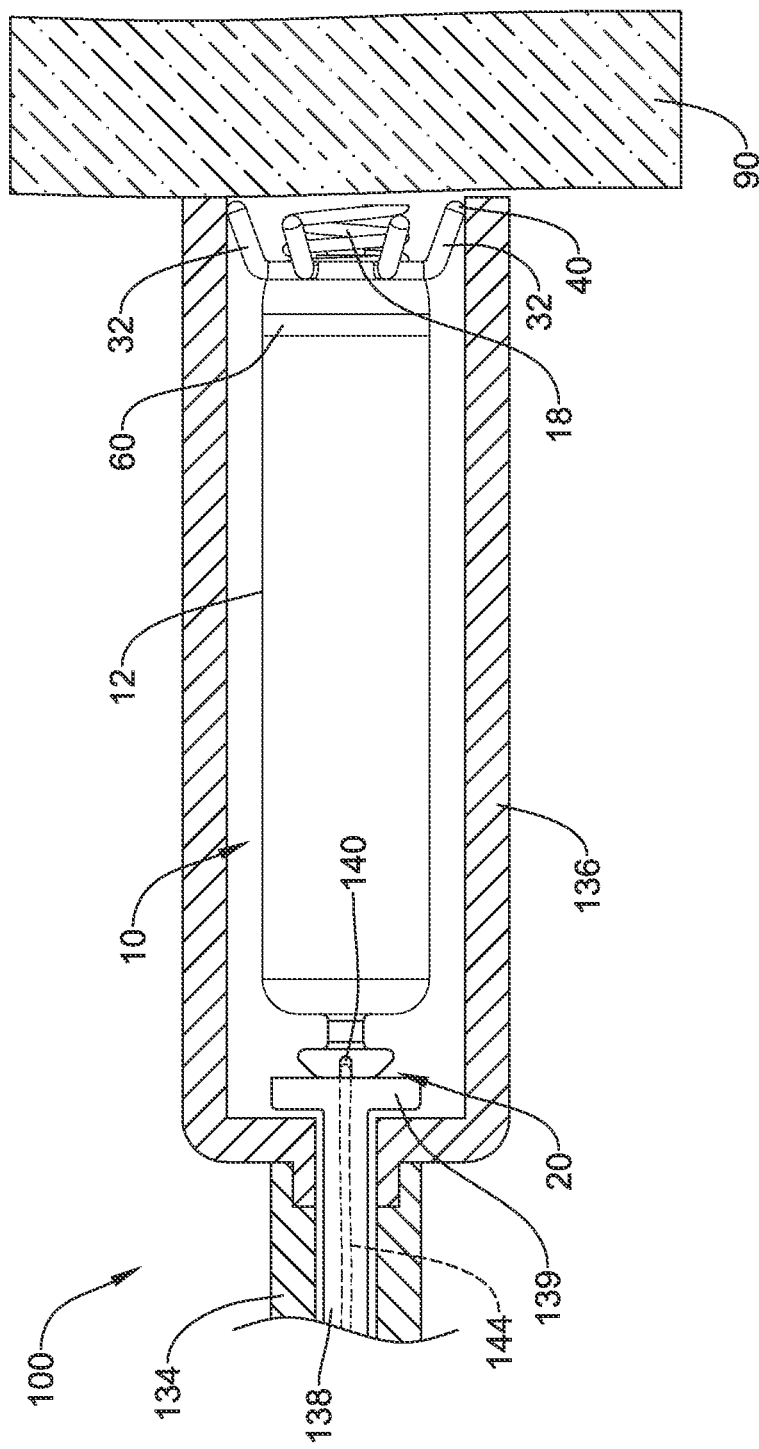
FIGS. 3A-3C illustrate aspects of an exemplary method of implanting the leadless pacing device shown in FIG. 2 into cardiac tissue using a delivery catheter.
Figure 3B:
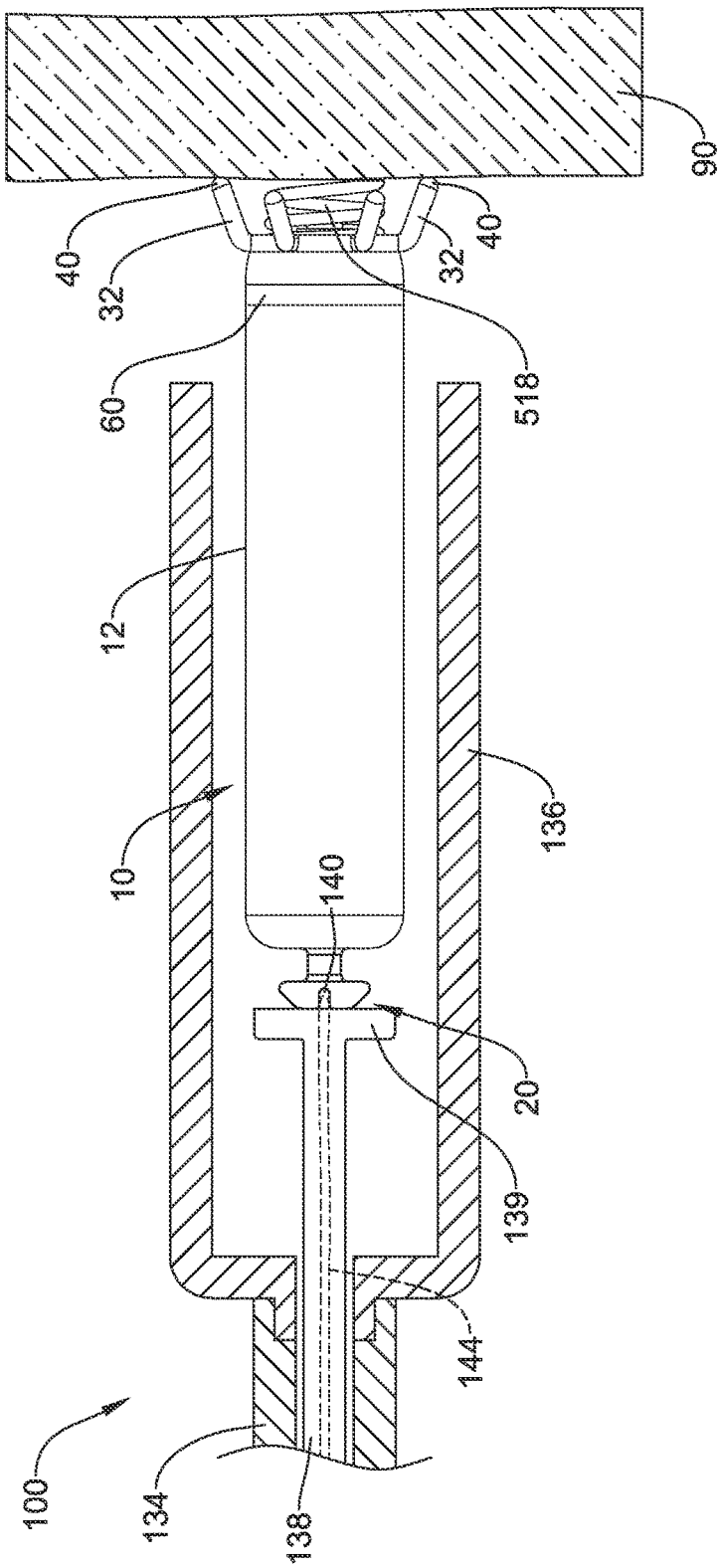
Figure 3C:
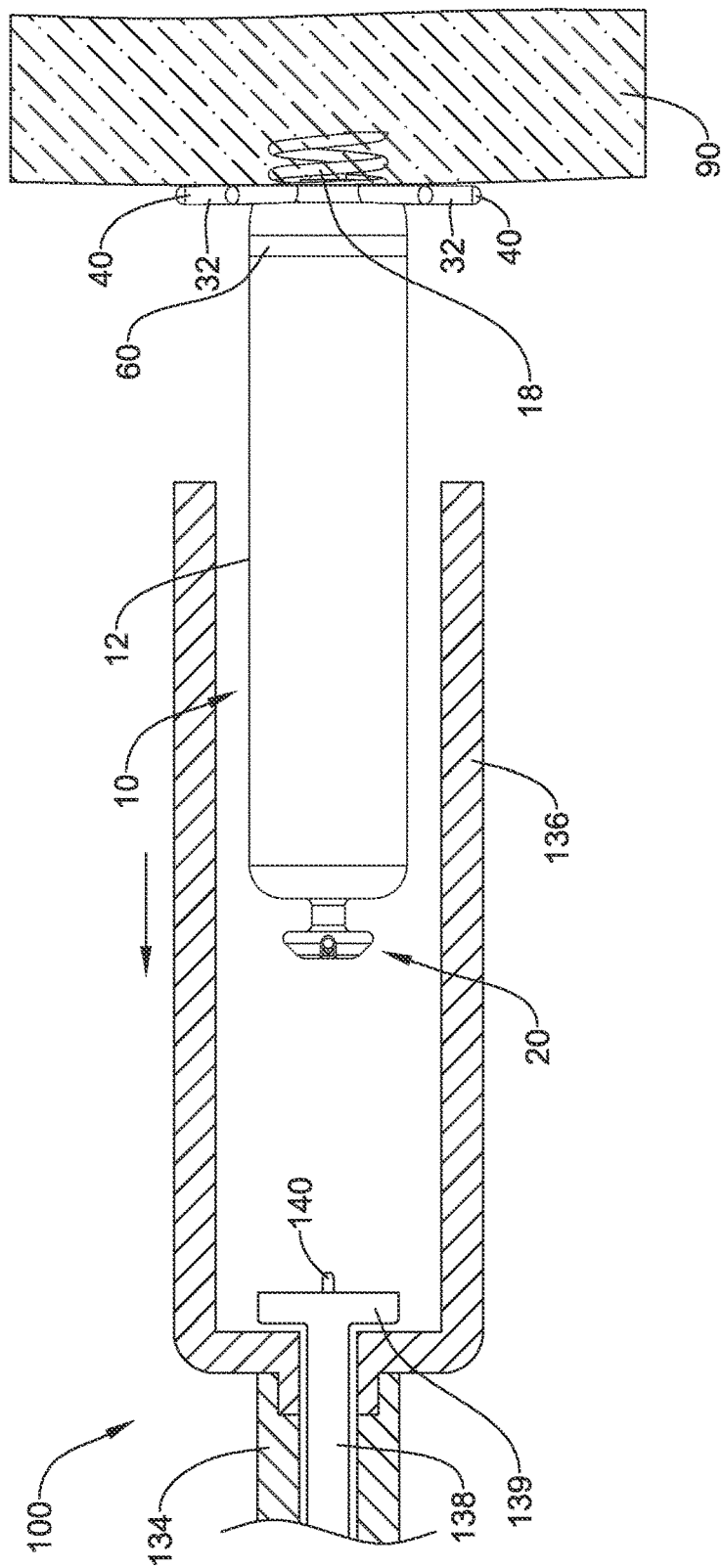

FIGS. 3A-3C illustrate aspects of an exemplary method of implanting the leadless pacing device shown in FIG. 2 into cardiac tissue using a delivery catheter 100. The catheter 100 may include a proximal member or region 134 and a distal member or holding section 136 configured to house the implantable device 10 during a delivery procedure. A push member 138 may be disposed (e.g., slidably disposed) within the proximal region 134. A distal or head region 139 of the push member 138 may be disposed within the distal holding section 136. The head region 139 may be capable of engaging the docking member 20 of the device 10. For example, the head region 139 may include one or more lugs 140 that are capable of engaging the bore 30 formed in the docking member 20. When the lugs 140 are engaged with the bore 30, the push member 138 may be rotated to thread or rotate the anchor member 18 into a target region 90 (e.g., a region of the heart such as the right ventricle). In some embodiments, a holding member or suture 144 may also extend through a lumen formed in the push member 138 and pass through the bore 30 so as to secure the device 10 to the delivery catheter 100 during portions or all of the delivery process.

The catheter 100 may be advanced through the vasculature to target region 90, with the device 10 positioned in the distal holding section 136 of the delivery catheter 100. For example, the catheter 100 may be advanced through a femoral vein, into the inferior vena cava, into the right atrium, through the tricuspid valve, and into the right ventricle. The target region 90 may be a portion of the right ventricle. For example, the target region 90 may be a portion of the right ventricle near the apex of the heart. In other instances, however, the target region 90 may be in another portion of the heart, such as in another chamber of the heart, for example.

The device 10 may include the anchor member 18 and tissue engagement verification features, such as the tines 32. During advancement of the catheter 100 through the vasculature, the tines 32 may be oriented in the distal direction (e.g., toward the distal end of the device 10 and/or distally from the device 10).

When the device 10 has been positioned proximate the target region 90, the device 10 may be expelled from the distal holding section 136, as shown in FIG. 3B. For example, the device 10 may be rotated with the push member 138 such that the anchoring member 18 screws into the target region 90 of cardiac tissue. As the anchoring member 18 is screwed into the target region 90, the distal ends of the tines 32 may engage the target tissue 90. Further rotation or screwing of the anchoring member into the target tissue 90 may cause the tines 32 to move (e.g., deflect) from the first position, shown in FIG. 3B to a second position, shown in FIG. 3C. As the tines 32 move (e.g., deflect) via engagement with the cardiac tissue 90, the free ends of the tines 32 may move toward the proximal end of the housing 12 as the tines 32 move from the first position to the second position. Visual observation of the movement of the radiopaque material, such as the radiopaque markers 40, of the tines 32 may provide intraoperative visual feedback via fluoroscopy during implantation of anchoring member 18 of the device 10 into the target region 90. In instances in which the device 10 includes a radiopaque reference point 60 which is stationary relative to the housing 12, displacement of the radiopaque material 40 of the tines 32 relative to the radiopaque reference point 60 may provide visual feedback of engagement of the tissue anchoring member 18 in the cardiac tissue 90. For example, medical personnel may confirm that the tissue anchoring member 18 is sufficiently anchored in the cardiac tissue 90 when the radiopaque material (e.g., radiopaque marker 40) of the tines 32 moves to a predetermined distance from the radiopaque reference point 60 at the second position. The predetermined distance may be less than the distance from the radiopaque reference point 60 at the first position.

FIGS. 4A and 4B illustrate another illustrative example of a tissue engagement verification feature 150 incorporated with the implantable leadless cardiac pacing device 10. Tissue engagement verification features 150 may be fixedly attached to the housing 12 of the device 10. In other words, the tissue engagement verification features 150 may be designed so that during typical use, the tissue engagement verification features 150 remain attached to housing 12. In some embodiments, the tissue engagement verification features 150 may have some freedom of movement relative to the housing 10. For example, the tissue engagement verification features 150 may be capable of pivoting, rotating, or otherwise moving relative to housing 12.

The form of the tissue engagement verification features 150 may vary. For example, the tissue engagement verification features 150 may take the form of a compressible member, such as an open wound coil 132. The open wound coil 132 is shown coaxial with the helical tissue anchoring member 18, with the open wound coil 132 surrounding the tissue anchoring member 18. However, in other embodiments, the open wound coil 132 may be positioned within the helical tissue anchoring member 18, or otherwise disposed. The open wound coil 132 may extend distally from the distal end of the housing 12, for example.

The open wound coil 132 may be constructed such that adjacent windings of the open wound coil 132 are spaced apart a first distance when in a first, uncompressed position, and move closer together with an applied force (e.g., a second, compressed position), such as upon engagement of the open wound coil 132 with cardiac tissue.

The open wound coil 132 may be doped with, made of, or otherwise include a radiopaque material. In some instances, only a discrete portion of the open wound coil 132 may include a radiopaque material, such as at a distal tip of the open wound coil 132, or along another portion of the open wound coil 132, and thus serve as a radiopaque marker. In other instances, the entire open wound coil 132 may be formed of a radiopaque material or be doped with a radiopaque material, and thus serve as a radiopaque marker. Radiopaque materials are understood to be materials capable of producing a relatively bright image on a fluoroscopy screen or another imaging technique during a medical procedure. This relatively bright image aids the user of the device 10 visualizing the radiopaque open wound coil 132 using fluoroscopy. Some examples of radiopaque materials can include, but are not limited to, gold, platinum, palladium, tantalum, tungsten alloy, polymer material loaded with a radiopaque filler, and the like.

In some instances, the device 10 may also include a radiopaque reference point which is stationary relative to the housing 12, or be included as part of the housing 12. Accordingly, displacement of the radiopaque open wound coil 132 relative to the radiopaque reference point of the housing 12 (e.g., compression of the open wound coil 132) may provide visual feedback of engagement of the tissue anchoring member 18 in cardiac tissue.

Figure 5A:
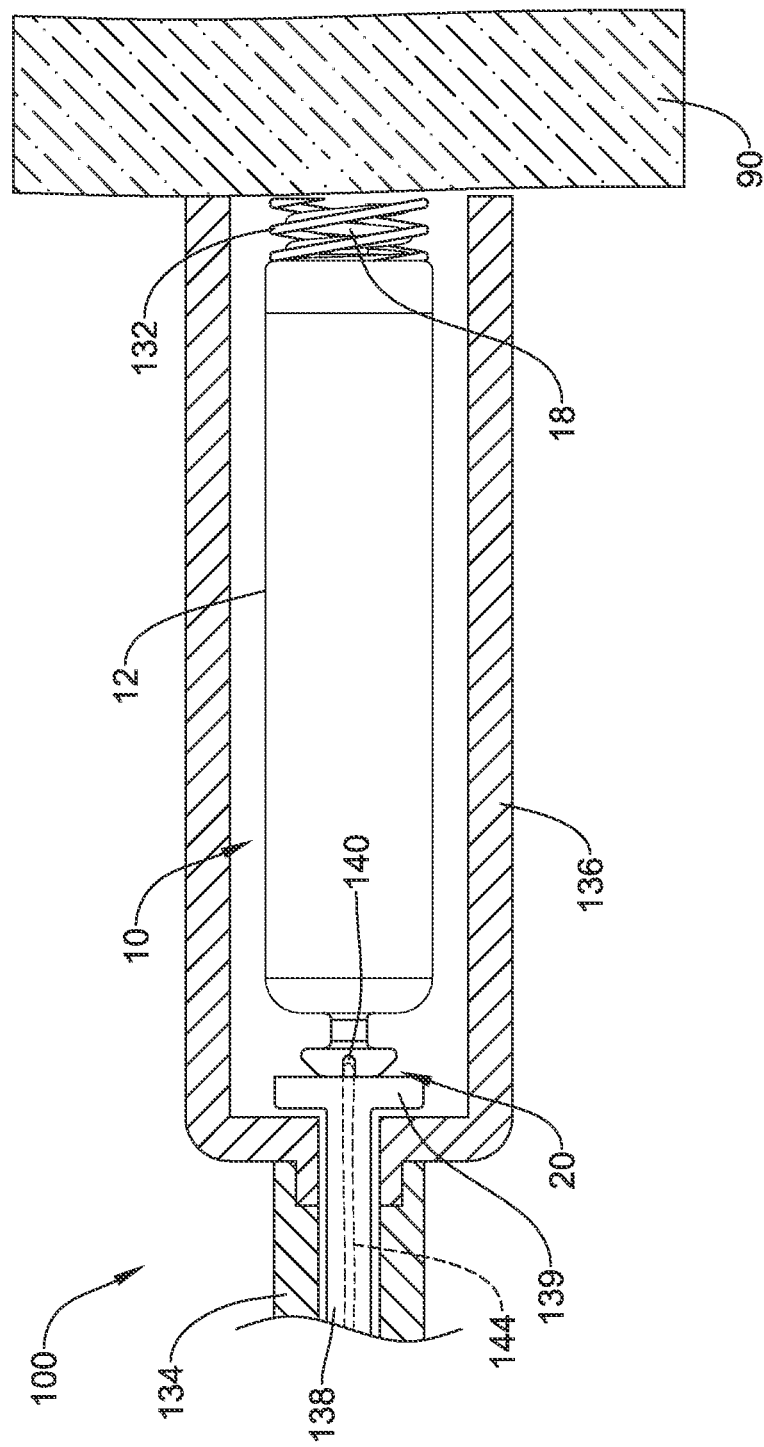
FIGS. 5A-5B illustrate aspects of an exemplary method of implanting the leadless pacing device shown in FIG. 4A into cardiac tissue using a delivery catheter.
Figure 5B:
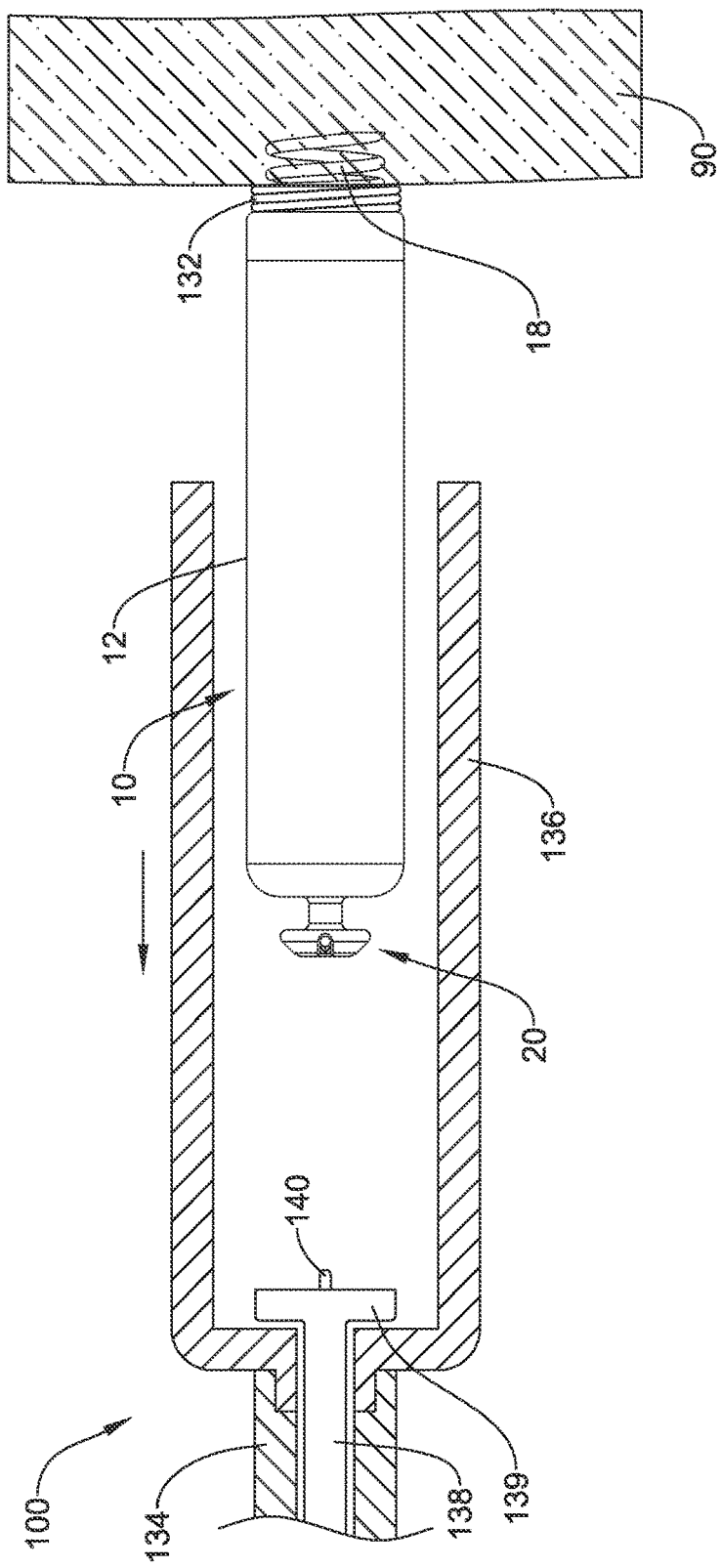

FIGS. 5A and 5B illustrate aspects of an exemplary method of implanting the leadless pacing device shown in FIGS. 4A and 4B into cardiac tissue using the delivery catheter 100. The delivery catheter 100, previously described above, may include a distal member or holding section 136 configured to house the implantable device 10 during a delivery procedure. Additional features of the delivery catheter 100 have been described above.

The catheter 100 may be advanced through the vasculature to target region 90, with the device 10 positioned in the distal holding section 136 of the delivery catheter 100. For example, the catheter 100 may be advanced through a femoral vein, into the inferior vena cava, into the right atrium, through the tricuspid valve, and into the right ventricle. The target region 90 may be a portion of the right ventricle. For example, the target region 90 may be a portion of the right ventricle near the apex of the heart. In other instances, however, the target region 90 may be in another portion of the heart, such as in another chamber of the heart, for example.

The device 10 may include the anchor member 18 and tissue engagement verification features, such as the open wound coil 132. During advancement of the catheter 100 through the vasculature, the open wound coil 132, which may extend distally from the distal end of the housing 12, may be in a first, uncompressed position with adjacent windings spaced from one another.

When the device 10 has been positioned proximate the target region 90, the device 10 may be expelled from the distal holding section 136, as shown in FIG. 5B. For example, the device 10 may be rotated with the push member 138 such that the anchoring member 18 screws into the target region 90 of cardiac tissue. As the anchoring member 18 is screwed into the target region 90, the distal end of the open wound coil 132 may engage the target tissue 90. Further rotation or screwing of the anchoring member into the target tissue 90 may cause the open wound coil 132 to compress from the first position, shown in FIG. 5A to a second, compressed position, shown in FIG. 5B. In some instances, the open wound coil 132 may be wound in an opposite direction than the helical tissue anchoring member 18 such that rotation of the device 10 with the distal end of the open wound coil 132 against the cardiac tissue 90 will not cause the open wound coil 132 to penetrate into the cardiac tissue 90, but rather remain against the surface of the cardiac tissue 90. As the distal end of the coil 132 moves proximally relative to the housing 12 (e.g., compresses) via engagement with the cardiac tissue 90, the spacing between adjacent windings of the open wound coil 132 will be reduced. Visual observation of the movement of the radiopaque material, such as the compression of the open wound coil 132, and thus the diminution of the spacing between adjacent windings, may provide intraoperative visual feedback via fluoroscopy during implantation of anchoring member 18 of the device 10 into the target region 90. For example, medical personnel may confirm that the tissue anchoring member 18 is sufficiently anchored in the cardiac tissue 90 when the open wound coil 132 is compressed a predetermined amount and/or the distal end of the open wound coil 132 moves proximally relative to the housing 12 a predetermined amount at the second position.

FIGS. 6A and 6B illustrate another illustrative example of a tissue engagement verification feature 250 incorporated with the implantable leadless cardiac pacing device 10. Tissue engagement verification features 250 may be fixedly attached to the housing 12 of the device 10. In other words, the tissue engagement verification features 250 may be designed so that during typical use, the tissue engagement verification features 250 remain attached to housing 12. In some embodiments, the tissue engagement verification features 250 may have some freedom of movement relative to the housing 10. For example, the tissue engagement verification features 250 may be capable of pivoting, rotating, or otherwise moving relative to housing 12.

The form of the tissue engagement verification features 250 may vary. For example, the tissue engagement verification features 250 may take the form of a compressible member, such as one or more, or a plurality of deflectable struts 232. The annular ring 240 is shown coaxial with the helical tissue anchoring member 18, with the annular ring 240 surrounding the tissue anchoring member 18. However, in other embodiments, the annular ring 240 may be positioned within the helical tissue anchoring member 18, or otherwise disposed. The struts 232 may extend distally from the distal end of the housing 12, for example. The struts 232 may have a proximal end secured to the housing 12 and a distal end secured to the annular ring 240, for example.

The struts 232 may be configured to deflect, bend, collapse, or otherwise be altered to move the ends of the struts toward one another, when subjected to an external force. The struts 232 may be formed of a flexible material. For example, the struts 232 may be made from a metal, metal alloy, polymer (some examples of which are disclosed below), a metal-polymer composite, combinations thereof, and the like, or other suitable material. Some examples of suitable metals and metal alloys include stainless steel, such as 304V, 304L, and 316LV stainless steel, a nickel-titanium alloy such as linear-elastic and/or super-elastic nitinol, other nickel alloys. Some examples of suitable polymers may include elastomeric polyamides, polyurethane, polyether block amide (PEBA, for example available under the trade name PEBAX®), ethylene vinyl acetate copolymers (EVA), silicones, polyethylene (PE), as well as other suitable materials, or mixtures, combinations, copolymers thereof, and the like.

The tissue engagement verification feature 250 may be constructed such that the distal ends of the struts 232 and/or the annular ring 240 is positioned a first distance from the distal end of the housing 12 when in a first, uncompressed position, and the distal ends of the struts 232 and/or the annular ring 240 is positioned a second distance (e.g., a second, compressed position), less than the first distance (e.g., moved proximally toward the distal end of the housing 12), with an applied force, such as upon engagement of the distal ends of the struts 232 and/or the annular ring 240 with cardiac tissue.

The struts 232 and/or the annular ring 240 may be doped with, made of, or otherwise include a radiopaque material, and thus serve as a radiopaque marker. For example, the annular ring 240 may be formed of a radiopaque material or be doped with a radiopaque material, and thus serve as a radiopaque marker. Radiopaque materials are understood to be materials capable of producing a relatively bright image on a fluoroscopy screen or another imaging technique during a medical procedure. This relatively bright image aids the user of the device 10 visualizing the radiopaque annular ring 240 using fluoroscopy. Some examples of radiopaque materials can include, but are not limited to, gold, platinum, palladium, tantalum, tungsten alloy, polymer material loaded with a radiopaque filler, and the like.

In some instances, the device 10 may also include a radiopaque reference point which is stationary relative to the housing 12, or be included as part of the housing 12. For example the radiopaque reference point 60 may be a radiopaque ring surrounding the housing 12, or another radiopaque structure on the housing 12, or the material forming the housing 12. Accordingly, displacement of the radiopaque material of the struts 232 and/or the annular ring 240 relative to the radiopaque reference point 60 may provide visual feedback of engagement of the tissue anchoring member 18 in cardiac tissue.

Figure 7A:
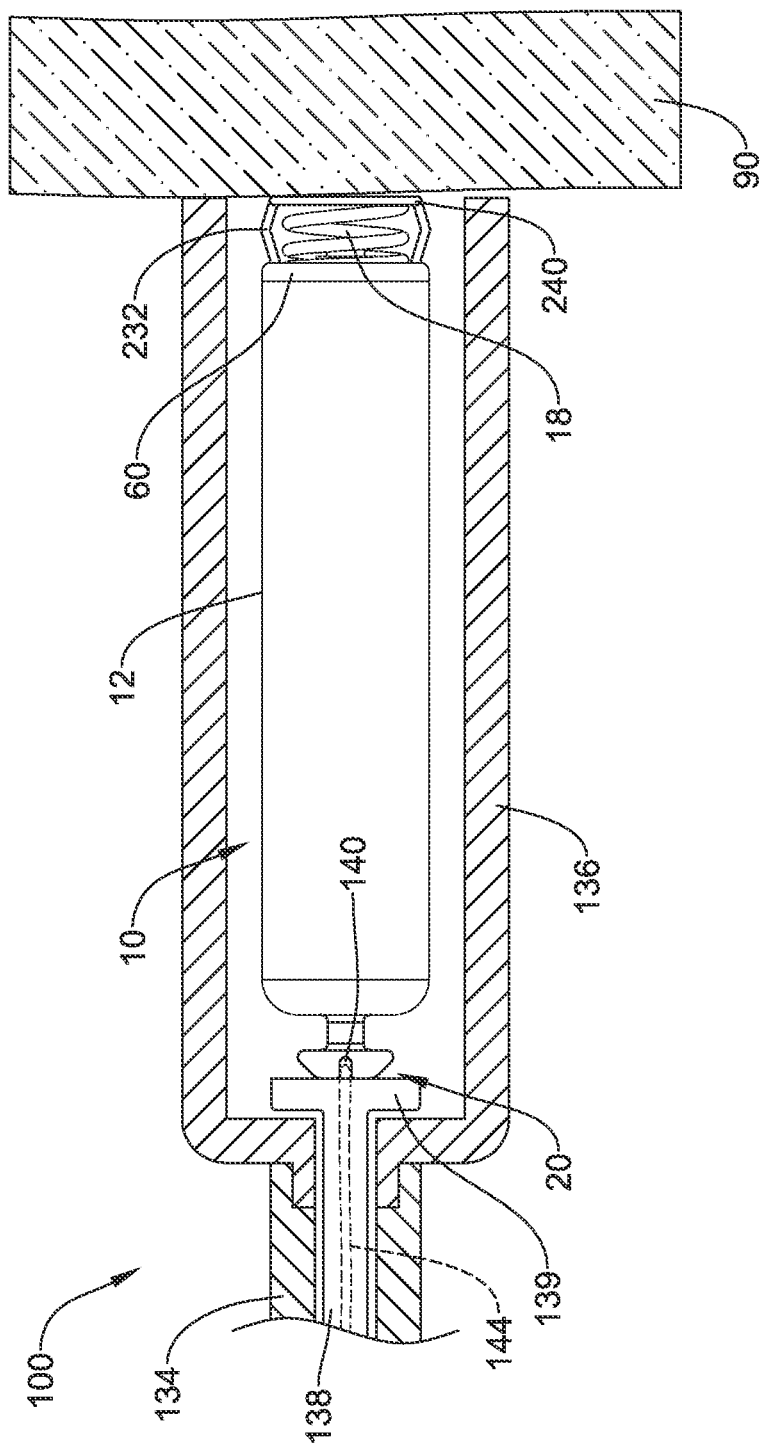
FIGS. 7A-7B illustrate aspects of an exemplary method of implanting the leadless pacing device shown in FIG. 6A into cardiac tissue using a delivery catheter.
Figure 7B:
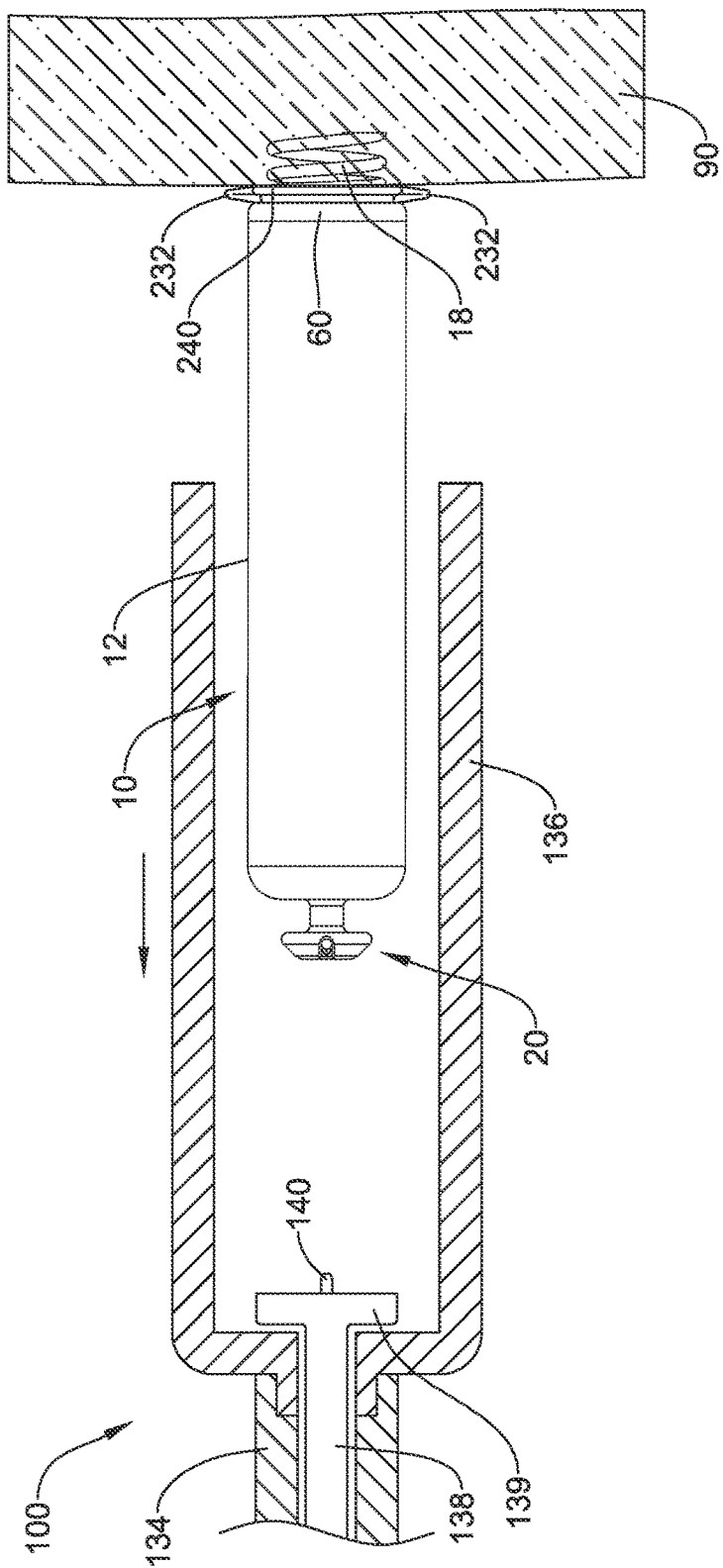

FIGS. 7A and 7B illustrate aspects of an exemplary method of implanting the leadless pacing device shown in FIGS. 6A and 6B into cardiac tissue using the delivery catheter 100. The delivery catheter 100, previously described above, may include a distal member or holding section 136 configured to house the implantable device 10 during a delivery procedure. Additional features of the delivery catheter 100 have been described above.

The catheter 100 may be advanced through the vasculature to target region 90, with the device 10 positioned in the distal holding section 136 of the delivery catheter 100. For example, the catheter 100 may be advanced through a femoral vein, into the inferior vena cava, into the right atrium, through the tricuspid valve, and into the right ventricle. The target region 90 may be a portion of the right ventricle. For example, the target region 90 may be a portion of the right ventricle near the apex of the heart. In other instances, however, the target region 90 may be in another portion of the heart, such as in another chamber of the heart, for example.

The device 10 may include the anchor member 18 and tissue engagement verification features, such as the tissue engagement verification feature 250 including the struts 232 and/or annular ring 240. During advancement of the catheter 100 through the vasculature, the struts 232, which may extend distally from the distal end of the housing 12, may be in a first, uncompressed position positioning the distal ends of the struts 232 and/or annular ring 240 a first distance from the distal end of the housing 12.

When the device 10 has been positioned proximate the target region 90, the device 10 may be expelled from the distal holding section 136, as shown in FIG. 7B. For example, the device 10 may be rotated with the push member 138 such that the anchoring member 18 screws into the target region 90 of cardiac tissue. As the anchoring member 18 is screwed into the target region 90, the distal end of the tissue engagement verification feature 250, such as the distal ends of the struts 232 and/or the annular ring 240, may engage the target tissue 90. Further rotation or screwing of the anchoring member into the target tissue 90 may cause the struts 232 to deflect, bend, collapse or otherwise be altered from the first position, shown in FIG. 7A to a second, compressed position, shown in FIG. 7B. As the distal ends of the struts 232 move proximally relative to the housing 12 (e.g., compress) via engagement with the cardiac tissue 90, the annular ring 240 will move closer to the distal end of the housing 12. Visual observation of the movement of the radiopaque material, such as the distal ends of the struts 232 and/or the annular ring 240, in relation to the radiopaque reference point (e.g., the housing 12 or a marker on the housing 12), may provide intraoperative visual feedback via fluoroscopy during implantation of anchoring member 18 of the device 10 into the target region 90. For example, medical personnel may confirm that the tissue anchoring member 18 is sufficiently anchored in the cardiac tissue 90 when the distal ends of the struts 232 and/or the annular ring 240 move proximally a predetermined amount to the second position, such that the distal ends of the struts 232 and/or the annular ring 240 are positioned a predetermined distance from the distal end of the housing 12.

Figure 8:
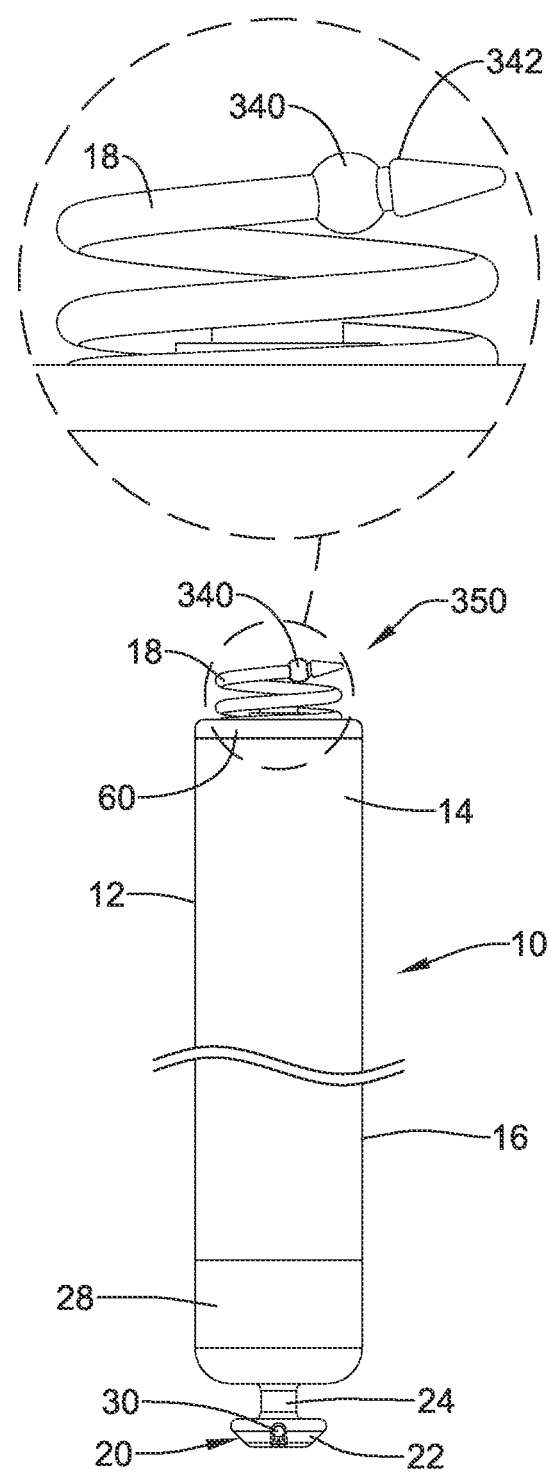
FIG. 8 is a side view of another exemplary leadless pacing device.

FIG. 8 illustrates another illustrative example of a tissue engagement verification feature 350 incorporated with the implantable leadless cardiac pacing device 10, such as incorporated with the helical anchoring member 18. The form of the tissue engagement verification feature 350 may vary. For example, the tissue engagement verification feature 350 may take the form of a movable member, such as a bead 340 slidably disposed on the helical anchoring member 18. The bead 340 is shown surrounding the helical tissue anchoring member 18. However, in other embodiments, the bead 340, or other movable member, may be otherwise slidably coupled to the helical tissue anchoring member 18, or otherwise disposed. In some instances, the helical tissue anchoring member 18 may include a stop 342 located distal of the bead 340 to prevent disengagement of the bead 340 from the tissue anchoring member 18. In some instances, the stop 342 may include an annular rim, a ridge, bump or other feature configured to contact the bead 340 at a distalmost end of travel of the bead 340 along the tissue anchoring member 18. The bead 340 may be configured to travel proximally along the helical anchoring member 18 from the distalmost end of travel defined by the stop 342.

The tissue engagement verification feature 350 may be constructed such that the bead 340 is positioned on the helical tissue anchoring member 18 at a first distance from the distal end of the housing 12 when in a first position, and the bead 340 is movable along the tissue anchoring structure 18 such that the bead 340 is positioned a second distance less than the first distance in a second position, as the tissue engagement member 18 is screwed into cardiac tissue.

The bead 340 may be doped with, made of, or otherwise include a radiopaque material, and thus serve as a radiopaque marker. For example, the bead 340 may be formed of a radiopaque material or be doped with a radiopaque material, and thus serve as a radiopaque marker. Radiopaque materials are understood to be materials capable of producing a relatively bright image on a fluoroscopy screen or another imaging technique during a medical procedure. This relatively bright image aids the user of the device 10 visualizing the radiopaque bead 340 using fluoroscopy. Some examples of radiopaque materials can include, but are not limited to, gold, platinum, palladium, tantalum, tungsten alloy, polymer material loaded with a radiopaque filler, and the like.

In some instances, the device 10 may also include a radiopaque reference point which is stationary relative to the housing 12, or be included as part of the housing 12. For example the radiopaque reference point 60 may be a radiopaque ring surrounding the housing 12, or another radiopaque structure on the housing 12, or the material forming the housing 12. Accordingly, displacement of the radiopaque bead 340 relative to the radiopaque reference point 60 may provide visual feedback of engagement of the tissue anchoring member 18 in cardiac tissue.

Figure 9A:
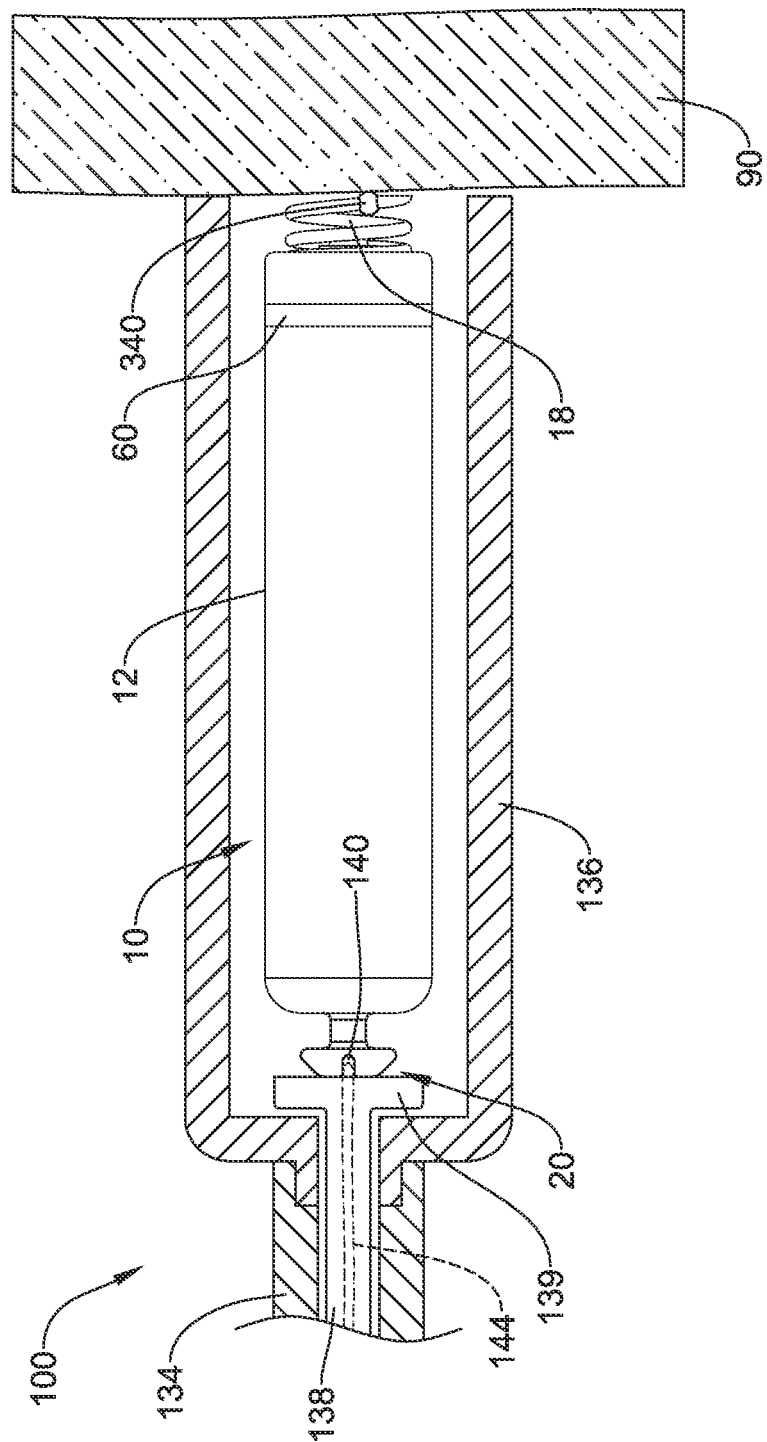
FIGS. 9A-9B illustrate aspects of an exemplary method of implanting the leadless pacing device shown in FIG. 8 into cardiac tissue using a delivery catheter.
Figure 9B:
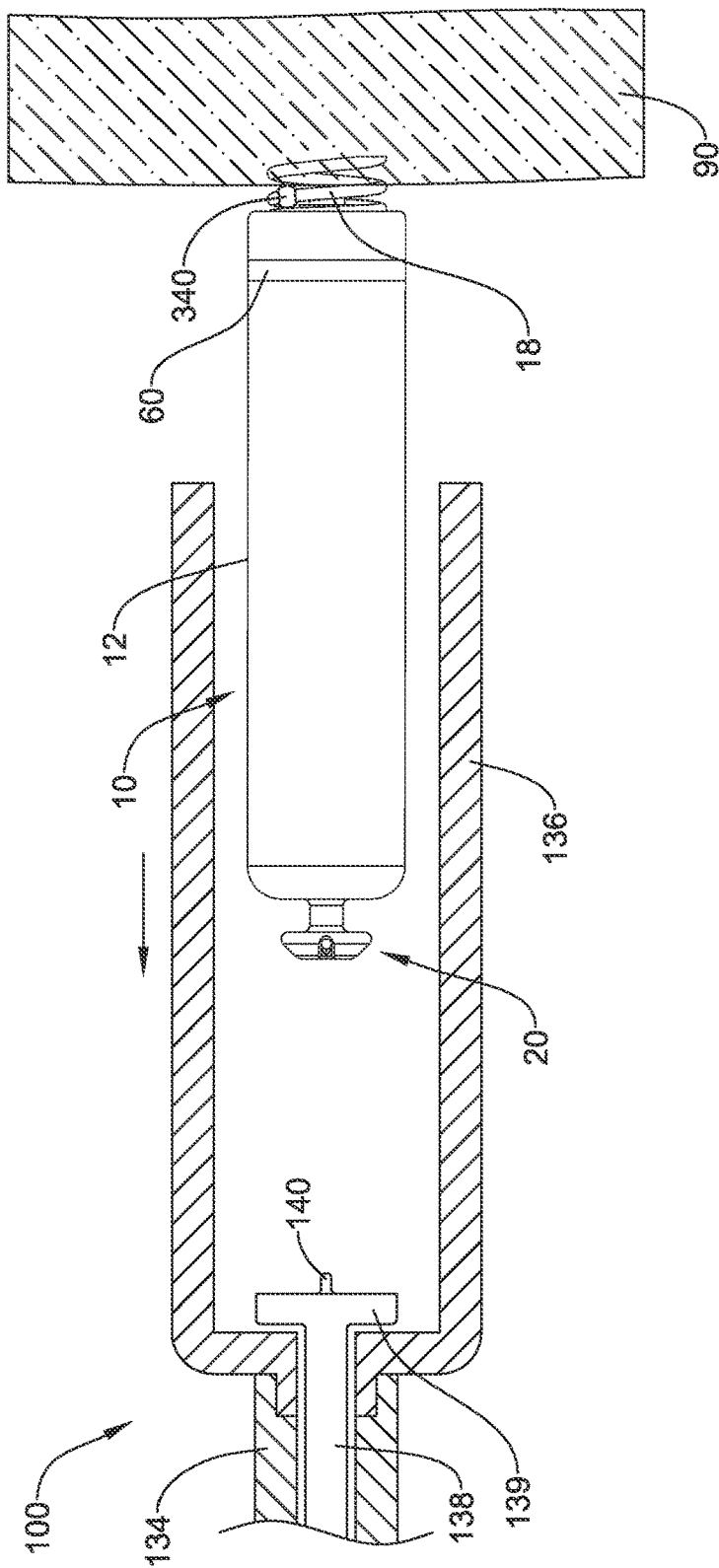

FIGS. 9A and 9B illustrate aspects of an exemplary method of implanting the leadless pacing device shown in FIG. 8 into cardiac tissue using the delivery catheter 100. The delivery catheter 100, previously described above, may include a distal member or holding section 136 configured to house the implantable device 10 during a delivery procedure. Additional features of the delivery catheter 100 have been described above.

The catheter 100 may be advanced through the vasculature to target region 90, with the device 10 positioned in the distal holding section 136 of the delivery catheter 100. For example, the catheter 100 may be advanced through a femoral vein, into the inferior vena cava, into the right atrium, through the tricuspid valve, and into the right ventricle. The target region 90 may be a portion of the right ventricle. For example, the target region 90 may be a portion of the right ventricle near the apex of the heart. In other instances, however, the target region 90 may be in another portion of the heart, such as in another chamber of the heart, for example.

The device 10 may include the anchor member 18 and tissue engagement verification features, such as the tissue engagement verification feature 350 including the bead 340 slidably coupled to the helical anchoring member 18. During advancement of the catheter 100 through the vasculature, the bead 340, which may be positioned proximate the stop 342, may be in a first position positioning the bead 340 a first distance from the distal end of the housing 12.

When the device 10 has been positioned proximate the target region 90, the device 10 may be expelled from the distal holding section 136, as shown in FIG. 7B. For example, the device 10 may be rotated with the push member 138 such that the anchoring member 18 screws into the target region 90 of cardiac tissue. As the anchoring member 18 is screwed into the target region 90, the bead 340 may engage the target tissue 90, and slide along the anchoring member 18. Further rotation or screwing of the anchoring member into the target tissue 90 may cause the bead 340 to move along the anchoring member 18 from the first position, shown in FIG. 9A to a second position, shown in FIG. 9B. As the anchoring member 18 is screwed into target tissue 90, the bead 340 moves proximally relative to the housing 12 along the anchoring member 18 via engagement with the cardiac tissue 90. Visual observation of the movement of the radiopaque material, such as the bead 340, in relation to the radiopaque reference point (e.g., the housing 12 or a marker 60 on the housing 12), may provide intraoperative visual feedback via fluoroscopy during implantation of anchoring member 18 of the device 10 into the target region 90. For example, medical personnel may confirm that the tissue anchoring member 18 is sufficiently anchored in the cardiac tissue 90 when the bead 340 moves proximally a predetermined amount to the second position, such that the bead 340 is positioned a predetermined distance from the distal end of the housing 12.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

Additional Examples

A first example is an implantable leadless cardiac pacing device including a housing having a proximal end and a distal end, an electrode positioned proximate the distal end of the housing configured to be positioned adjacent cardiac tissue, and a tissue anchoring member extending from the distal end of the housing configured to secure the housing to cardiac tissue. The device further includes a tissue engagement verification feature configured to provide feedback upon engagement of the tissue anchoring member in cardiac tissue.

Additionally or alternatively, in a second example, the tissue engagement verification feature is movable from a first position relative to the housing to a second position relative to the housing.

Additionally or alternatively, in a third example, the first position is an equilibrium position, and the second position is a displaced position through application of an external force.

Additionally or alternatively, in a fourth example, the tissue engagement verification feature moves toward the proximal end of the housing as the tissue engagement verification feature moves from the first position to the second position.

Additionally or alternatively, in a fifth example, the tissue engagement verification feature includes a radiopaque material to provide visual feedback via fluoroscopy.

Additionally or alternatively, in a sixth example, the radiopaque material is movable relative to the housing.

Additionally or alternatively, a seventh example includes radiopaque reference point which is stationary relative to the housing, wherein displacement of the radiopaque material relative to the radiopaque reference point provides visual feedback of engagement of the tissue anchoring member in cardiac tissue.

Additionally or alternatively, in an eighth example, the tissue engagement verification feature includes one or more tines configured to deflect upon engagement with cardiac tissue.

Additionally or alternatively, in a ninth example, the tissue engagement verification feature includes a compressible member configured to compress upon engagement with cardiac tissue.

Additionally or alternatively, in a tenth example, the compressible member includes an open wound coil.

Additionally or alternatively, in an eleventh example, adjacent windings of the open wound coil move closer together upon engagement of the open wound coil with cardiac tissue.

Additionally or alternatively, in a twelfth example, the compressible member includes one or more deflectable struts.

Additionally or alternatively, in a thirteenth example, the one or more deflectable struts extend between the distal end of the housing to a ring comprising a radiopaque material.

Additionally or alternatively, in a fourteenth example, the tissue engagement verification feature includes a radiopaque member configured to move along the tissue anchoring member upon engagement with cardiac tissue.

Additionally or alternatively, in a fifteenth example, the radiopaque member includes a bead slidable along tissue anchoring member.

What is claimed is:

1. An implantable leadless cardiac pacemaker comprising:
    a housing having a proximal end and a distal end;
    an electrode positioned proximate the distal end of the housing configured to be positioned adjacent cardiac tissue and stimulate the cardiac tissue;
    a helical tissue anchor extending from the distal end of the housing configured to be implanted in the cardiac tissue to secure the housing to the cardiac tissue; and
    a tissue engagement indicator distinct from the helical tissue anchor, the tissue engagement indicator being movable relative to the helical tissue anchor and the housing to provide feedback of a degree of engagement of the helical tissue anchor in the cardiac tissue.

2. The implantable leadless cardiac pacemaker of claim 1, wherein the tissue engagement indicator is movable from a first position relative to the housing to a second position relative to the housing.

3. The implantable leadless cardiac pacemaker of claim 2, wherein the first position is an equilibrium position, and the second position is a displaced position through application of an external force.

4. The implantable leadless cardiac pacemaker of claim 3, wherein the tissue engagement indicator moves toward the proximal end of the housing as the tissue engagement indicator moves from the first position to the second position.

5. The implantable leadless cardiac pacemaker of claim 1, wherein the tissue engagement indicator includes a radiopaque material to provide visual feedback via fluoroscopy.

6. The implantable leadless cardiac pacemaker of claim 5, wherein the radiopaque material is movable relative to the helical tissue anchor and the housing.

7. The implantable leadless cardiac pacemaker of claim 6, further comprising a radiopaque reference point which is stationary relative to the housing, wherein a distance of displacement of the radiopaque material relative to the radiopaque reference point provides visual feedback of the degree of engagement of the helical tissue anchor in the cardiac tissue.

8. The implantable leadless cardiac pacemaker of claim 1, wherein the tissue engagement indicator includes one or more tines configured to deflect upon engagement with the cardiac tissue.

9. The implantable leadless cardiac pacemaker of claim 1, wherein the tissue engagement indicator is configured to compress upon engagement with the cardiac tissue.

10. The implantable leadless cardiac pacemaker of claim 9, wherein the tissue engagement indicator comprises an open wound coil.

11. The implantable leadless cardiac pacemaker of claim 10, wherein adjacent windings of the open wound coil move closer together upon engagement of the open wound coil with the cardiac tissue.

12. The implantable leadless cardiac pacemaker of claim 9, wherein the tissue engagement indicator comprises one or more deflectable struts.

13. The implantable leadless cardiac pacemaker of claim 12, wherein the one or more deflectable struts extend between the distal end of the housing to a ring comprising a radiopaque material.

14. The implantable leadless cardiac pacemaker of claim 1, wherein the tissue engagement indicator includes a radiopaque marker configured to move along the tissue anchor upon engagement with the cardiac tissue.

15. The implantable leadless cardiac pacemaker of claim 14, wherein the radiopaque marker includes a bead slidable along the tissue anchor.

16. An implantable leadless cardiac pacemaker comprising:
 a housing having a proximal end and a distal end;
 an electrode positioned proximate the distal end of the housing configured to be positioned adjacent cardiac tissue and stimulate the cardiac tissue;
 a helical tissue anchor extending from the distal end of the housing configured to be implanted in the cardiac tissue to secure the housing to the cardiac tissue; and
 a radiopaque marker distinct from the helical tissue anchor and movable relative to the housing and the helical tissue anchor; and
 a radiopaque reference point disposed on the housing and stationary relative to the housing;
 wherein a distance of displacement of the radiopaque marker relative to the radiopaque reference point provides visual feedback of a degree of engagement of the helical tissue anchor in the cardiac tissue.

17. The implantable leadless cardiac pacemaker of claim 16, wherein the radiopaque marker is movable toward the proximal end of the housing as the helical tissue anchor engages the cardiac tissue.

18. The implantable leadless cardiac pacemaker of claim 17, wherein the radiopaque marker is movable from a first position relative to the housing to a second position relative to the housing;
 wherein the first position is an equilibrium position, and the second position is a displaced position through application of an external force.

19. A method of implanting a leadless cardiac pacemaker having a housing, the method comprising:
 advancing the leadless cardiac pacemaker into a chamber of a heart;
 engaging a helical tissue anchor of the leadless cardiac pacemaker into cardiac tissue;
 fluoroscopically observing a distance of displacement of a radiopaque marker of the leadless cardiac pacemaker relative to a radiopaque reference point disposed on the housing to confirm engagement of the helical tissue anchor in the cardiac tissue and verify a degree of tissue engagement of the helical tissue anchor with the cardiac tissue;
 wherein the radiopaque marker is distinct from the helical tissue anchor and is moveable relative to the helical tissue anchor and the housing.

20. The method of claim 19, wherein the radiopaque marker moves toward a proximal end of the housing as the tissue anchor is engaging the cardiac tissue.

* * * * *